United States Patent [19]
Quiachon et al.

[11] Patent Number: 6,039,743
[45] Date of Patent: Mar. 21, 2000

[54] GUIDE WIRE HAVING DISTAL EXTREMITY WITH ADJUSTABLE SUPPORT CHARACTERISTIC AND METHOD

[75] Inventors: Dignah B. Quiachon, Mountain View; Deepak R. Gandhi, San Jose; Dennis L. Brooks, Windsor; Mir A. Imran, Los Altos Hills; Roger J. Guidi, Los Altos, all of Calif.

[73] Assignee: Intella Interventional Systems, Inc., Sunnyvale, Calif.

[21] Appl. No.: 08/902,772

[22] Filed: Jul. 30, 1997

Related U.S. Application Data

[62] Division of application No. 08/585,885, Jan. 11, 1996, Pat. No. 5,697,380.

[51] Int. Cl.[7] .......................... A61F 11/00; A61M 29/00
[52] U.S. Cl. .......................... 606/108; 606/191; 604/280
[58] Field of Search .......................... 606/108, 191–200; 623/1, 11, 12; 604/280; 600/434, 585

[56] References Cited

U.S. PATENT DOCUMENTS

| | | |
|---|---|---|
| 5,055,101 | 10/1991 | McCoy .......................... 604/95 |
| 5,213,111 | 5/1993 | Cook et al. . |
| 5,234,451 | 8/1993 | Osypka .......................... 606/159 |
| 5,449,369 | 9/1995 | Imran .......................... 606/159 |
| 5,458,605 | 10/1995 | Klemm .......................... 606/108 |
| 5,542,434 | 8/1996 | Imran et al. . |
| 5,779,722 | 7/1998 | Shturman et al. .......................... 606/159 |

*Primary Examiner*—Glenn K. Dawson
*Attorney, Agent, or Firm*—Flehr Hohbach Test Albritton & Herbert LLP

[57] ABSTRACT

A guide wire having a distal extremity with an adjustable support characteristic including a core wire having proximal and distal extremities. The distal extremity has a reduced cross sectional area which is more flexible than the proximal extremity. A tip is secured to the distal extremity of the core wire. A sleeve of superelastic material is disposed coaxially on the distal extremity of the core wire. The sleeve is annealed so that it is relatively flexible at a temperature ranging from 20° to 40° C. and becomes progressively stiffer as temperature increases. The core wire conducts electrical energy to the superelastic sleeve to supply heat to the sleeve and extends from the proximal extremity of the core wire to the sleeve to cause the sleeve to become stiffer to thereby increase the stiffness of the distal extremity of the guide wire. A guide wire is provided having a distal extremity with an adjustable support characteristic which varies from a floppy characteristic to a stiff characteristic.

1 Claim, 1 Drawing Sheet

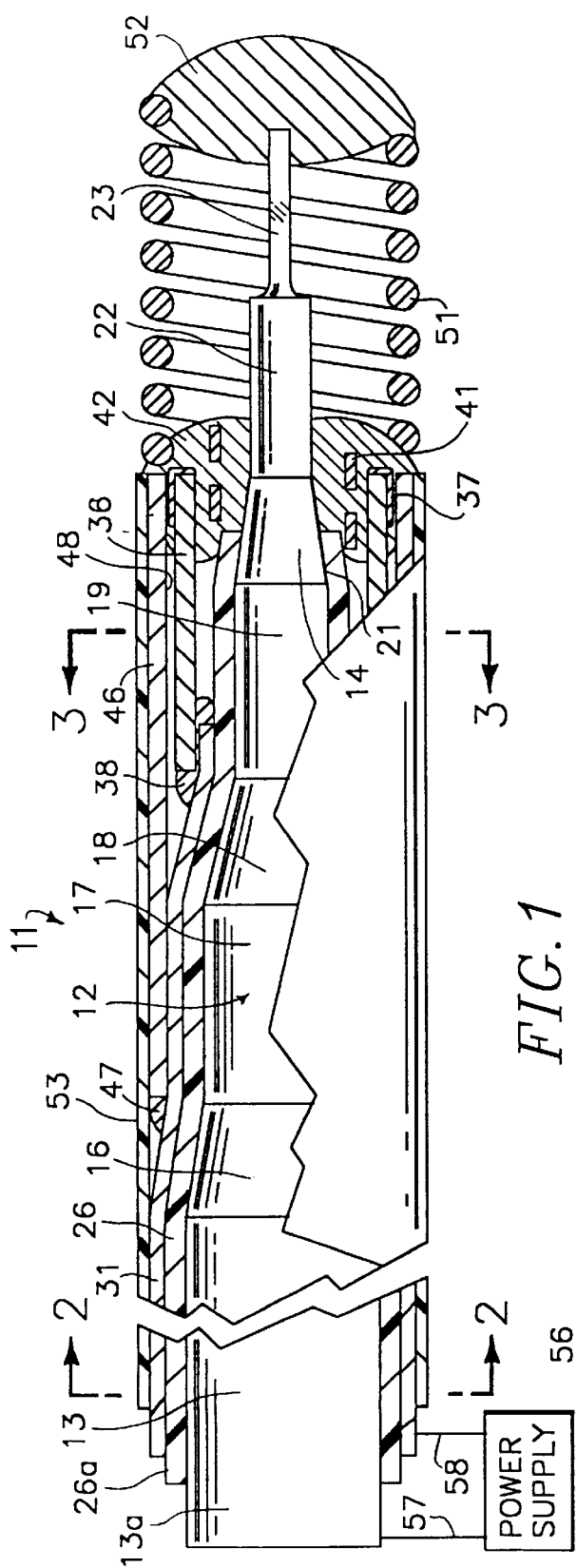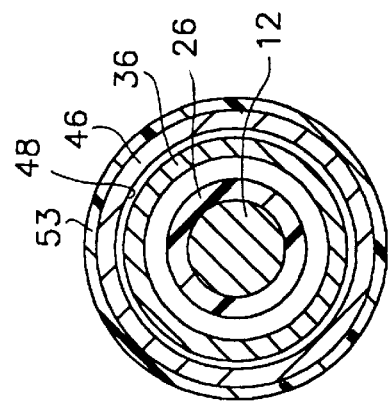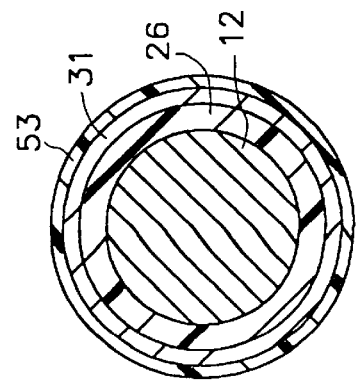

GUIDE WIRE HAVING DISTAL EXTREMITY WITH ADJUSTABLE SUPPORT CHARACTERISTIC AND METHOD

This is a division, of application Ser. No. 08/585,885, filed Jan. 11, 1996, now U.S. Pat. No. 5,697,380.

This invention relates to a guide wire having a distal extremity with an adjustable support characteristic and method and more particularly to such a guide wire which can be utilized for help in delivering a stent.

Guide wires have heretofore been provided. Heretofore such guide wires which have been utilized for helping deliver stents have been provided with a stiffer distal extremity in order to achieve the stiffness required to place the stent in the desired location. When such a guide wire is provided with such stiffness, it is difficult to utilize such a guide wire for initially entering the vessel. This is true because with such guide wires it typically has been desirous that the tips be very floppy so that they can negotiate tortuosities encountered in the vessel. This often has made it necessary to utilize two guide wires in a single procedures one guide wire being utilized having a floppy distal extremity for directing the guide wire into the desired location after which the floppy guide wire is removed and the other guide wire having a stiffer distal extremity being utilized for positioning a stent in the desired location. There therefore is a need for providing a guide wire which can have a very floppy distal extremity and which can thereafter be made stiffer to aid in positioning a stent in the desired location.

In general, it is an object of the present invention to provide a guide wire having a distal extremity with an adjustable support characteristic and method.

Another object of the invention is to provide a guide wire of the above character in which a sleeve of a superelastic material is provided at the distal extremity making it possible to adjust the stiffness of the distal extremity.

Another object of the invention is to provide a guide wire of the above character which initially can have a very floppy distal extremity.

Another object of the invention is to provide a guide wire of the above character which can be utilized to aid in delivering a stent.

Another object of the invention is to provide a guide wire of the above character in which the stiffness of the distal extremity can be increased to facilitate delivery of a stent.

Another object of the invention is to provide a guide wire of the above character which can be adjusted to provide additional support to aid in delivering a stent and which does not readily collapse or prolapse and does not resist placement of a stent delivery catheter.

Another object of the invention is to provide a guide wire and method of the above character which only requires the use of one guide wire during an angioplasty procedure even though a stent may be placed during the angioplasty procedure.

Additional objects and features of the invention will appear from the following description in which the preferred embodiments are set forth in detail in conjunction with the accompanying drawings.

FIG. 1 is a side elevational view partially in section of a guide wire having a distal extremity with an adjustable support characteristic.

FIG. 2 is a cross sectional view taken along the line 2—2 of FIG. 1.

FIG. 3 is a cross sectional view taken along the line 3—3 of FIG. 1.

In general, the guide wire having a distal extremity with an adjustable support characteristic comprised of a core wire having proximal distal extremities. The distal extremity has a reduced cross sectional area to provide a distal extremity which is more flexible than the proximal extremity of the core wire. Means is provided which forms a tip secured to the distal extremity of the core wire. A sleeve of superelastic material is coaxially disposed on the distal extremity of the core wire sleeve and is relatively flexible at a temperature ranging from 20° C. to 40° C. and generally becomes progressively stiffer as temperature increases. Conductor means is provided which is carried by the core wire for conducting electrical energy to the sleeve and extends from the proximal extremity of the core wire to the sleeve for causing heating of the sleeve to cause it to become stiffer to thereby increase the stiffness of the distal extremity of the guide wire.

More in particular, the guide wire 11 having a distal extremity with an adjustable support characteristic consists of a core wire 12 having proximal and distal extremities 13 and 14. It is formed of a suitable solid conductive material such as 304V stainless steel. It can have a suitable length ranging from 150 to 175 centimeters and preferably a length of approximately 160 centimeters. It can have a diameter ranging from 0.010" to 0.018" and larger if desired but preferably a diameter of 0.012". The distal extremity 14 is provided with a plurality of transitions to smaller sizes. These transitions can extend over a suitable length as for example 25 centimeters from the distal most extremity of the guide wire 12. The distal extremity 14 is of reduced cross section to provide a distal extremity which is more flexible than the proximal extremity of the core wire 12. Thus there is provided a first transition or taper 16 to a portion 17 having a diameter of 0.095" extending for a distance of approximately 6 centimeters followed by another taper or transition 18 in which the diameter is reduced to 0.007" to a portion 19 extending for a distance of approximately 6 centimeters to another taper or transition 21 to a portion 22 having a diameter of 0.0025" and having a length of approximately 2–3 centimeters, the distal extremity of which has been flattened to provide a portion 23 having a suitable cross-sectioned area such as 0.0012" by 0.005".

After the core wire has been centerless ground and formed in the manner hereinbefore described, it is coated with a layer 26 of a suitable insulating material such as a polyimide to form a sleeve which extends from the proximal extremity 13 of the guide wire leaving a small portion 13a of the proximal extremity exposed for making an electrical connection as hereinafter described and extending over the taper 16, the portion 17, the taper 18, the portion 19 and a small portion of the taper 21 as shown in FIG. 1. The polyimide sleeve 26 can have a suitable thickness as for example from 0.0005" to 0.002" and preferably a thickness of 0.001".

Typically in manufacture, the entire surface of the core wire 12 is coated with a polyimide and then the proximal extremity, about ⅜" in length of the core wire 12 is stripped of the polyimide coating and similarly the distal most extremity of the core wire 12 extending proximally 4–5 centimeters is stripped. After the polyimide layer has been formed in the appropriate manner, a conductive layer 31 is provided which extends over the polyimide layer 26. The conductive layer 31 is formed of a suitable material such as a silver ink having a wall thickness ranging from 0.0005" to 0.002" and preferably about 0.001". As shown in FIG. 1, the conductive silver ink layer 31 terminates near the proximal extremity of the polyimide insulating layer 26 to leave a small portion 26a exposed as shown. The conductive layer 31 extends over the taper 16, the portion 17, the taper 18 and a small part of the portion 19 as shown in FIG. 1.

A tube 36 of a superelastic material, often called Nitinol, is mounted coaxially on the distal extremity 14 of the core wire 12 and has a length ranging from 10 to 12 centimeters and an inner diameter of between 0.009" and 0.010", an outside diameter ranging from 0.011" to 0.012" to provide a wall thickness ranging from 0.001" to 0.0015". In one embodiment of the present invention, the sleeve had a wall thickness of 0.0025" that was thinned down to a thickness ranging from 0.001" to 0.0015" by centerless grinding after which the sleeve was cut down to the desired length and the edges rounded. Thereafter a mandrel of a suitable material such as stainless steel having the desired sizes inserted into the sleeve 36. The mandrel is used to keep the tube or sleeve 36 straight and circular rather than oval-shaped or elliptical so that it will not deform during annealing as hereinafter described. Thus the mandrel can have an outside diameter of for example 0.0085" to 0.009". The sleeve with the mandrel therein is placed in a conventional oven and heat treated for a period of time ranging from 20 to 30 minutes and preferably for approximately 25 minutes at a temperature ranging from 430 to 450° C. and preferably 440° C. After this annealing operation has been completed, the superelastic sleeve 36 is removed from the oven and permitted to cool after which the mandrel is removed. Prior to the annealing operation, the sleeve was relatively rigid whereas after the annealing operation hereinbefore described, the sleeve is very flexible and pliable. As is well known to those skilled in the art of superelastic materials, the elastic material before annealing was in the austenitic phase at room temperature whereas by the heat treatment it was transformed into the martensitic phase at room temperature. Thus by the annealing step hereinbefore described, the superelastic material was transformed from the austenitic phase to the martensitic phase so it is quite floppy and flexible at room temperature and will only assume the austenitic phase and become stiff when subjected to heat as hereinafter described.

After the sleeve 36 has been annealed as hereinbefore described, the distal extremity of the sleeve or tube 36 is dipped for a distance of 5 millimeters in a molten metal such as silver to provide a silver layer 37 within the distal mouth of the sleeve on tube 36. The sleeve or tube 36 is then slipped over the distal extremity 14 of the core wire 12. As can be seen from FIG. 1, the distal extremity of the sleeve comes in contact with and overlies the silver ink layer 31 to make good electrical contact between the silver plating 37 and the conductive layer 31. The purpose of the silver plating 37 is to optimize electrical contact of the distal end of the Nitinol sleeve to the stainless steel core because Nitinol is difficult to solder. Also, in order to assure that a good electrical contact is made, a silver epoxy 38 is applied at the proximal extremity of the sleeve 36 and over the conductive layer 31. This can most appropriately be accomplished by placing a dab of the silver epoxy over the area of the conductive layer 31 to be engaged by the sleeve 36 and then slowly rotating the sleeve 36 while putting it in a place so that there is a concentric distribution of the epoxy 37 on the conductive layer 31 to assure that a good electrical contact has been made. The silver epoxy can be cured at room temperature or curing can be accelerated by the application of heat in a manner well known to those skilled in the art.

In order to assure good electrical contact with the distal extremity of the Nitinol tube or sleeve 36, a low conductivity spring 41 having at least two turns as shown in FIG. 1 is positioned within the distal extremity of the Nitinol sleeve 36 and retained therein by suitable means such as a silver solder 42 to thereby make good electrical contact between the core wire 12 and the distal extremity of the Nitinol sleeve 36. The coil 41 is formed of a flat silver wire having cross sectional area 0.004" and a thickness of 0.001".

An insulating sleeve 46 formed of a suitable material such as a polyimide is provided and has an inside diameter of approximately 0.0123" and an outside diameter of 0.0138". This insulating sleeve 46 is slid over the Nitinol sleeve 36 and extends proximally of the Nitinol sleeve over the conductive layer 31 and has its proximal extremity secured to the conductive layer 31 by a suitable adhesive 47 such as cyanoacrylate to hold it in place. The distal extremity of the insulating sleeve 46 is trimmed so that it is flush and lines up with the distal extremity of the Nitinol tube 36. The insulating sleeve 46 provides thermal insulation for the Nitinol sleeve or tube 36 when it is activated as hereinafter described. It also serves to prevent the blood from acting as a heat sink when the guide wire is disposed in blood in a vessel during a medical procedure.

As shown in FIG. 1, the insulating sleeve 46 is sized so that it provides an annular space 48 which provides additional thermal insulation.

A radiopaque coil 51 is provided and is formed of a suitable radiopaque material such as platinum or a tungsten platinum alloy having a length and ranging from 3 to 4 centimeters having an outer diameter of 0.014" with the individual turns of the coil 51 having a cross sectional diameter of approximately 0.0025". The proximal and of the coil 51 is soldered to the silver-plated distal extremity of the Nitinol sleeve 36 as well as to the coil spring 41 by the solder 42. The flattened portion 23 of the core wire 12 is secured to the distal extremity of the radiopaque coil 51 by a silver solder indicated at 52 to provide a rounded generally hemispherical atraumatic tip for the guide wire.

If desired, as shown in the drawings a lubricous coating 53 of a suitable such as Teflon can be applied to the exterior surface of the guide wire 11 to enhance the capability of the guide wire 11 to transverse vessels in the patient. The coating 53 can have a thickness ranging from 0.0005" to 0.001".

Operation and use of the guide wire 11 with adjustable support characteristic may now be briefly described as follows. At room temperature, the distal extremity of the guide wire 11 is very floppy and has characteristics comparable to floppy guide wires presently in the marketplace. Let it be assumed that it is desired to perform a conventional angioplasty procedure in which an entry is made into the femoral artery of the patient and a guiding catheter is inserted therein. Thereafter, the guide wire 11 of the present invention is introduced to the coronary vessel of the patient through the guiding catheter in a conventional manner utilizing the floppy characteristics of the guide wire to pass through tortuosities if present in the vessel until the distal extremity is disposed in the stenosis or occlusion in the vessel. A conventional balloon catheter (not shown) can then be advanced over the guide wire 11 after it has been positioned in the desired location with the balloon catheter tracking the guide wire until the balloon has been advanced into the stenosis to be treated in the angioplasty procedure. The balloon of the balloon dilatation catheter can then be inflated one or more times to enlarge the opening through the stenosis.

Thereafter, let it be assumed that it is desired to place a stent in the stenosis so that to aid it in remaining open and so that restenosis will not occur, the balloon dilatation catheter can be removed leaving the guide wire in place. A stent delivery catheter is then advanced over the guide wire 11.

In order to provide additional support for the stent delivery catheter, electrical energy is supplied to the Nitinol sleeve 36 from a power supply 56 that is connected by a conductor 57 to the core wire 12 and to the conductive layer 31 by a conductor 58 to supply electric current directly to the Nitinol sleeve 36 to heat the same to a temperature above 60° C. but below 100° C. so that the superelastic material in the Nitinol sleeve is transformed to the austenitic state to progressively stiffen the same as the temperature increases and to thereby progressively stiffen the distal extremity of the guide wire 11. This stiffening serves to prevent the distal extremity of the guide wire from collapsing or prolapsing. The stent (not shown) is delivered into the stenosis by the stent delivery catheter. After the stent has been advanced over the stiffened guide wire 11, the stent can be positioned in a conventional manner and left in place and the stent delivery catheter can be removed after which the guide wire 11 also can be removed to complete the medical procedure.

By using the guide wire of the present invention, it is only necessary to utilize one guide wire because the guide wire has a distal extremity with an adjustable support characteristic in that it can be very floppy at room temperature or at the temperature of the human body when in blood in a vessel. It can be stiffened to provide additional support during the time it is desired to deliver a stent by supplying electrical energy to the Nitinol sleeve 36 to heat the same. It should be appreciated that if desired, rather than supplying electrical energy directly to the stent, electrical energy can be supplied to a heating element (not shown) either on the inside or on the outside of the sleeve to heat the same to also cause it to assume an austenitic or stiff characteristic.

Thus, it can be seen with the guide wire of the present invention, it is possible to reduce the cost and the time required for an angioplasty procedure in which a stent is to be deployed.

What is claimed:

1. A method for delivering a stent into a stenosis in a vessel in a patient by the use of a stent delivery catheter and a single guide wire having an adjustable support characteristic ranging from floppy to stiff comprising advancing the guide wire in the vessel of the patient while its distal extremity is floppy until the distal extremity has been advanced into the stenosis in the vessel which is to be treated, stiffening the distal extremity of the guide wire, advancing the stent delivery catheter over the guide wire while the distal extremity is stiff, advancing the stent into the stenosis and withdrawing the stent delivery catheter and the guide wire from the vessel of the patient.

* * * * *